US00PP11615P

United States Patent [19]

Probasco

[11] Patent Number: Plant 11,615

[45] Date of Patent: Nov. 7, 2000

[54] HOP PLANT NAMED 'H900325-5'

[75] Inventor: Gene Probasco, Yakima, Wash.

[73] Assignee: John I. Haas, Inc., Yakima, Wash.

[21] Appl. No.: 08/777,606

[22] Filed: Dec. 31, 1996

[51] Int. Cl.[7] ..... A01H 5/00

[52] U.S. Cl. ..... Plt./100

[58] Field of Search ..... Plt./100

[56] References Cited

U.S. PATENT DOCUMENTS

| | | | |
|---|---|---|---|
| P.P. 8,812 | 6/1994 | Probasco | Plt./100 |
| P.P. 8,823 | 7/1994 | Probasco | Plt./100 |
| P.P. 8,824 | 7/1994 | Probasco | Plt./100 |
| P.P. 9,511 | 4/1996 | Tanikoshi et al. | Plt./100 |

OTHER PUBLICATIONS

John I. Haas Co., Inc. "Farming" 1987 30 pages.
John I. Haas Co., Inc. "U.S. Hop Industry Information Manual" 1985 13 pages.
John I. Haas Co., Inc. "Hop Research & Development" 1989 9 pages.
John I. Haas Co., Inc. "Hop Pellets–Regular and Concentrated/Technical Data" 1985 9 pages.
John I. Haas Co., Inc. "Non–Isomerized Hop Extract–Technical Data" 1985 13 pages.
John I. Haas Co., Inc. "Isomerized Hop Extract–Technical Data" 1985 9 pages.
John I. Haas Co., Inc. "Hop Varieties–U.S. Grown" 8 pages.

*Primary Examiner*—James R. Feyrer
*Assistant Examiner*—Kent L. Bell
*Attorney, Agent, or Firm*—Morgan, Lewis & Bockius

[57] ABSTRACT

A new and distinct variety of hop, *Humulus lupulus L.*, characterized by a semi-dwarf stature and named 'H900323-5', has an unusually high percentage of alpha-acids in its resin, early maturity and a resonable projected cone yield on low trellis. The new variety was cultivated as a result of a cross at a greenhouse in Yakima, Wash., United States, and has been asexually reproduced in Yakima, Wash., United States.

3 Drawing Sheets

BACKGROUND AND SUMMARY OF INVENTION

Hops are grown commercially for use in flavoring beers, stouts and ales. Lupulin glands found inside female hop cones provide the resins and essential oils which are the primary components of the hop flavor each variety imparts to beers, stouts and ales. New hop varieties are evaluated for their growing characteristics, per acre hop cone yields (dried to approximately 8% moisture), the chemical composition of the resins and essential oils contained within the hop cone's lupulin glands, and the unique flavor each variety imparts to beers, stouts and ales. Only female hop plants produce cones containing lupulin glands, and thus only female hop plants have any commercial value. Male hop plants have no commercial value other than for use in breeding programs to create new varieties.

This invention relates to a new and distinct variety of hop and more particularly to an asexually reproduced hop variety selected from among hop plants resulting from a controlled cross pollination between an unpatented tetraploid USDA 21055 (non commercial breeding line) female hop plant with unpatented John I. Haas, Inc. (Haas) male hop plant No. 833-53M.

Haas male hop plant No. 833-53M originated from a controlled cross pollination in 1982 between unpatented female hop plant USDA Accession No. 21055 and unpatented male hop plant USDA Accession No. 63015M.

The controlled cross pollination program resulting in the creation of the new hop variety, hereafter called H900325-5 was performed in 1989 by Mr. Gene Probasco, a botanist employed by John I. Haas, Inc., in a Haas greenhouse located at 1112 North 16th Avenue, Yakima, Wash., 98902. Mr. Probasco discovered the H900325-5 variety in 1990 among the hop plants which were produced from the seeds resulting from the above described controlled cross pollination program.

The seeds from the cross between tetraploid USDA 21055 female hop plant and Haas male hop plant No. 833-53M were planted in a Haas greenhouse in 1990. The most vigorous plants resulting from the cross were selected and planted in a Haas hop field located at Wada Farm, Yakima Golding Farms, Toppenish, Wash. This planting did not produce a crop during the planting year.

In 1991, because of the chemical analysis and field observations of the hop plants resulting from the tetraploid USDA 21055 female×Haas male 833-53M cross, Mr. Probasco was attracted to the 'H900325-5' hop plant for its unusually high percentage of alpha-acids, early maturity and a reasonable projected per acre cone yield on low (10 foot) trellis. The per acre cone yield projections were based upon the cone production of the single 'H900325-5' hop plant observed in 1991.

It was noted that 'H900325-5' produced a sufficient number of very heavy cones for the height of the plant. The shortened internodes, laterals and overall plant height indicated that the plant could be described as a "semi-dwarf".

In 1992, the 'H900325-5' plant was observed again in the same location and production of alpha-acids was again high. This same year a larger scale trial consisting of thirty plants was planted at the John I. Haas, Inc. hop farm in Mabton, Wash. on a trial "low trellis" for the purpose of a small scale yield trial. These thirty plants constituted the first asexual reproduction of the 'H900325-5' variety taking place in a Haas greenhouse in Yakima, Wash. These plantings represented the second generation and did not produce a crop during the planting year. Additionally in 1992, a small scale trial consisting of three plants was established in Oregon.

In 1993 and 1994 the second generation plants in the trial at Mabton were harvested for chemical analysis and yield evaluations.

Results from the test plot provided additional information supporting the per acre cone yield and alpha-acids projections made from the original 'H900325-5' plant selected in 1991; confirmed the unusually high alpha-acids percentage characteristics of the new variety; and initiated the accumulation of historical agronomic data on the new variety.

In 1994, third generation rootstock from the 'H900325-5' variety was planted in a test plot of approximately 2.0 acres (large acreage test plot) at the John I. Haas, Inc. hop farm located at Mabton, Wash. Also, a small scale test plot of 150 plants was planted in Toppenish, Wash. Neither of these plantings yielded a crop in 1994.

In 1995, the two acre test plot of third generation plants at the Mabton farm was harvested using a mechanical field stripper designed for low trellis hop harvesting. Cleaning and drying of the harvested hops was in the conventional harvesting facility. The first year per acre cone production was approximately 984 pounds per acre. This is within the range of first year per acre cone production for a commercially viable hop variety. It is important to note that first year per acre cone yields in Washington State typically are lower than normal per acre yields for Washington State hop fields in subsequent years. Consequently, the per acre cone yield observations made from this first year one acre test plot were used to merely project anticipated normal yields for the new variety. The analytical data from chemical analysis of multiple random samples from bales of cones harvested from the two acre test plot showed an average alpha-acids percentage of 18.8% (ASBC spectrophotometric method). This is an unusually high alpha-acids percentage, and in combination with the early maturity and resonable yield on low trellis is one of the primary novel characteristics of this new variety.

In 1996, the two acre test plot produced 1740 pounds per acre and alpha-acids content was 19.4% (ASBC spectrophotometric method).

All of the testing and evaluation of the 'H900325-5' variety's growing characteristics, per acre hop cone yield and analytical data were carried out on hop farms and laboratory facilities which are wholly owned and controlled by John I. Haas, Inc.

No brewing for any beers, stouts or ales had been completed on this new variety as of the end of the 1996 growing season.

Based upon the field observations performed, and chemical analytical data collected during this testing and evaluation program from 1991 through 1996, it appears that second and third generation 'H900325-5' hop plants demonstrate genetic stability with respect to the new variety's novel characteristic of unusually high alpha-acids yields. Also, the new 'H900325-5' variety demonstrates genetic stability with respect to the production of commercially viable per acre hop cone yields.

The variety 'H900325-5' is usually ready to pick by the 15th to the 18th of August. This is approximately one week earlier than the variety Early Cluster. The compact and ovoid shape cones of this variety are mid to large in size and this aids in the ease of picking and cleaning. Commercial picking of plants grown on low trellis is done by a mechanical harvester which straddles the trellis and strips the cones and leaves of the laterals in an upward motion. Adaptation to this type of harvesting is very good, leaves do not develop in the cones, the cones detach easily from stems, and the cones do not shatter during commercial harvesting and drying.

This new hop variety has been carefully compared to its female parent, the unpatented USDA noncommercial breeding line 21055. The hop industry does not make or rely on any comparisons between new varieties and their male parents because male hops plants have no commercial value. The primary difference between the new 'H900325-5' variety and its female parent is the earliness of harvesting, semi-dwarf characteristics and the unusually high alpha-acids percentages in bales of harvested hop cones.

THE DRAWINGS

The accompanying four photographs illustrate the cones, leaves and short stature of the new 'H900325-5' variety:

DESCRIPTION OF THE VARIETY

Figure 1:
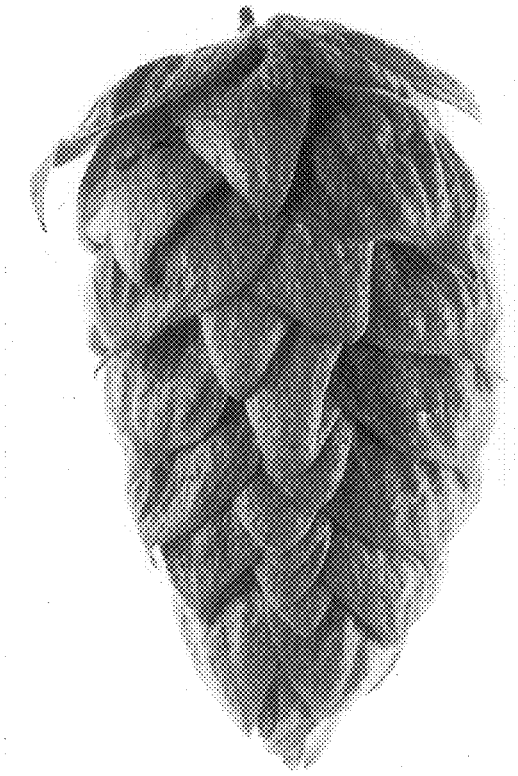
FIG. 1 depicts a close up of a single cone.

This description contains information about all botanical and analytical chemical characteristics upon which the hop industry relies in identifying and distinguishing specific hop varieties. The analytical data used to describe this new variety are subject to some variation among different samples of this new variety, due to the maturity of the hop cones sampled, climatic and growing conditions, geography, and other variables. For these reasons the analytical values used to describe this new variety are expressed in terms of ranges or averages of values rather than absolute or fixed values.

General Descriptive Information

I. Introduction

The hop plant, *Humulus lupulus L.,* is a perennial plant which produces annual climbing bines and a perennial crown. In the spring, the buds which have developed on the crown send out numerous shoots. The annual shoots are referred to as bines or vines and can grow up to 25 feet in a single growing season. The variety 'H900325-5' is a semi-dwarf and therefore grows to a height of only 12–14 feet. The bines climb in a clockwise direction without the aid of tendrils, but rather with the aid of hooked hairs known as tricomes. The bine of a mature hop may be one half to three quarters of an inch thick at the six foot height. Laterals grow from the axillary buds at each node along the main bine. The inflorescences develop from the axils of the laterals and each inflorescence becomes a single hop cone at maturity.

II. Crown

Much of the hop crown consists of branched stem tissue which lies buried at a shallow depth below the surface of the soil. This stem tissue, or rhizome, produces buds which in the spring develop into a mass of heterophyllous shoots. The hop crown will become woody with age, developing heavy, rough bark after the first year.

III. Roots

The crown produces two types of roots: horizontal and vertical. The horizontal roots are fibrous, absorptive roots used for water uptake. The vertical roots, which develop from the horizontal roots, are thick and fleshy and serve as carbohydrate storage organs.

IV. Stems

The annual stems grow from the crown in early spring and twine around suitable support. Shoots of 'H900325-5' emerge from winter dormancy approximately 1–2 weeks later than the commercial variety Galena. Galena emerges approximately the last week of March or first week of April in the state of Washington in the USA. Initial stem or shoot growth rate is slower than average, and overall growth appears shortened due to shorter internode length of the semi-dwarf stature. After spring pruning, growth becomes slower than average when compared to other commercial varieties such as Galena. The stems are hexagonal in shape with the corners of the hexagon often protruding. The main stem color is green and has no stripe. On all sides of the stem are hairs, consisting mostly of silicates, and as these harden they become one or two sided hooks. Generally, the size of the stem at the six foot height is between ¼" and ⅜" in diameter.

"Training" is a term used by growers which means placement of the annual stems (shoots, vines) on a support. The helical growth habit of the plant causes the plant to climb the support strings to the top of the trellis. Low trellis is the term which specifically relates to the height of the trellis system on which the hop plants are grown. Low trellis height stands at 10 feet, compared to the normal trellis height of 18 feet. There are no overhead cross wires in a low trellis system. This allows the harvesting of a low trellis variety with a portable field combine that straddles the 10' trellis. Different cultural practices are utilized for optimizing plant growth on low trellis compared to "high trellis" fields. The differences are aimed at reducing growing costs.

Figure 3:
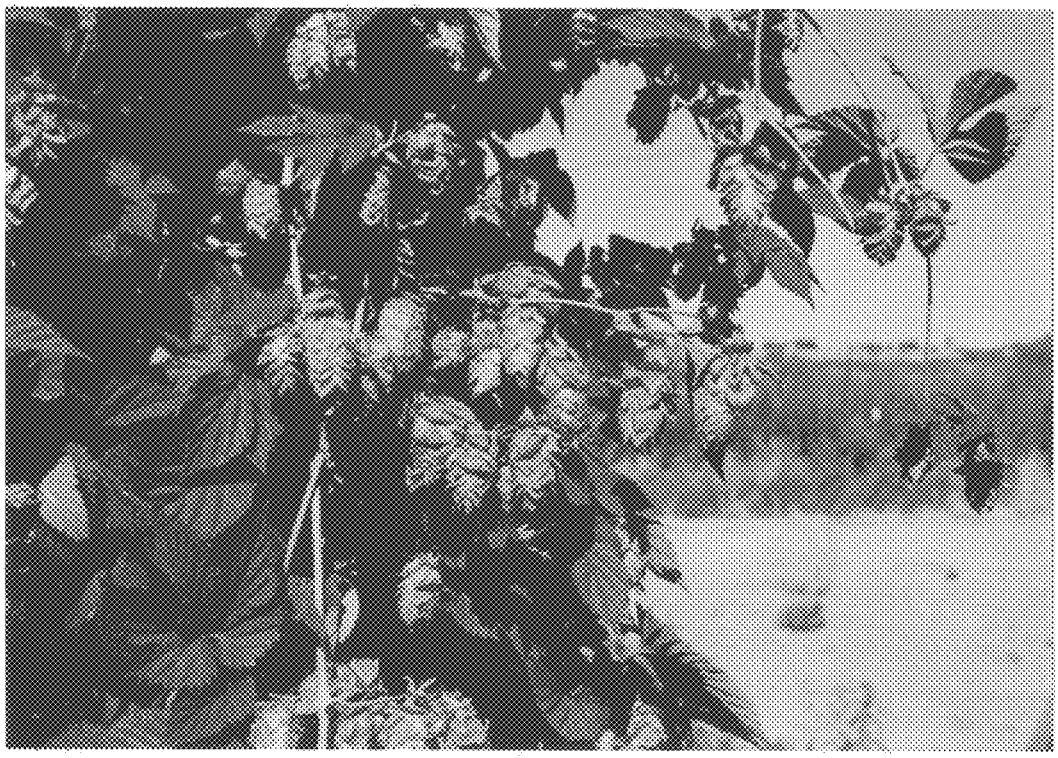
FIGS. 3 and 4 depict the appearance of the plants and cones as they are growing in the field on low trellis and approaching harvest time.
Figure 4:
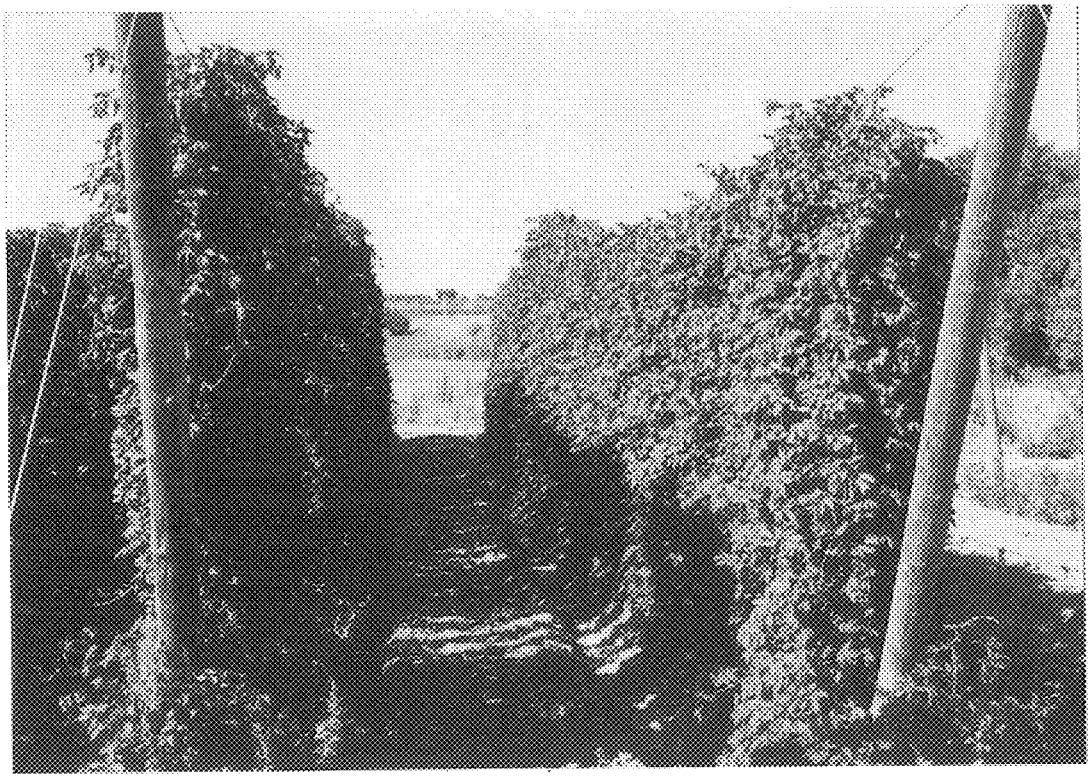

Low trellis vines are normally allowed to "self train" meaning that the vines are allowed to grasp the support strings to begin upward growth rather than to be manually wrapped around the support with the aid of human hands. The strings on which the hops are self-trained in the early spring are permanent, only being replaced every four to five years. 'H900325-5' has good vigor and can reach the top of the 10 foot high low trellis in 5–6 weeks after self training in mid-May, as depicted in FIGS. 3 and 4.

Pruning in the spring is timed to allow training to be accomplished by self-training at a much later time than would occur with high trellis manual training.

Harvesting is by mechanical strippers which straddle the 10' high rows and strip the leaves and cones from the vines. Cones are separated from the leaves at the stationary picking facility and dried by the usual methods.

V. Leaves

Figure 2:
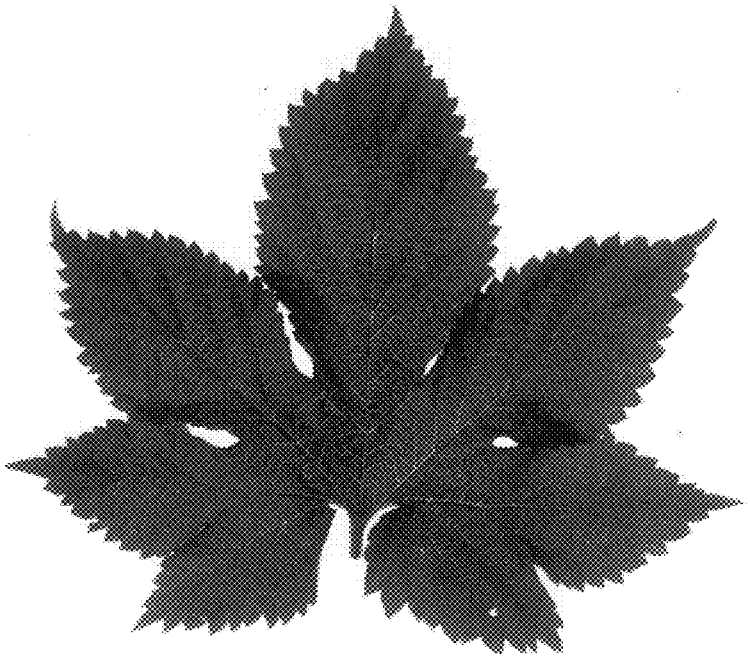
FIG. 2 depicts the leaf close up.

Leaves of 'H900325-5' are borne in pairs at each node on the main bine and the majority of these leaves are opposite in arrangement. Located at the petiole base of each leaf is a stipule which is interpetiolar in arrangement. 'H900325-5' leaves are small, as shown in FIG. 2, with the main bine leaves being approximately 6 inches wide. The bine leaves are cordate in shape with 3 to 5 palmate lobes, but mainly 5 lobes, and have palmate venation. The sinus cleft are deeply cut with leaf margins being smooth. The remainder of the leaf margins are serrate to dentate. Leaf color is a darker green on the upper surface than on the lower surface. Stiff fine hairs on the upper surface of the leaf produce a dull appearance and rough texture. The lower surface bears many disc-shaped yellowish resin glands. The leaves are petiolate and the petioles are slightly channeled, therefore having a flat surface on the upper side. The upper side of the petiole displays a purple shading. The leaf petiole extends from the main bine in a reflexed position.

VI. Laterals

The laterals, or sidearms as they are often called, originate from buds in the axils of leaves of the main bine. The lateral position is "caulous" which means it grows more or less evenly spaced along the main bine. Length of laterals and internode on the laterals of 'H900325-5' are shorter than those of most commercial varieties. The typical length ranges from 6"–24".

VII. Cones

The inflorescence of 'H900325-5' begin to appear in mid June and mature during the third week of August. As they mature, they form a conelike structure, or strobile, referred to as a "cone", which is shown in FIG. 1. These inflorescences develop on a cranked axis and the cones form in pairs or clusters. The cones develop on the laterals from the top of the plant to approximately 18 inches above the ground. The cone consists of a central rachis or strig which bears numerous bracts and bracteoles. At the base of each bracteole is an ovary which if fertilized by pollination, results in the lengthening and thicknening of the central strig. Plants of the variety 'H900325-5' cannot be fertilized because their genetic make up is triploid.

The aroma of hop cones of any variety is not measurable and therefore aroma descriptions are highly subjective. The aroma of 'H900325-5' can be described as strong but pleasant.

The hop cone of 'H900325-5' is ovoid to conic in shape and is tight when referring to its compactness. The tip of the cone is pointed. The bract tip shape is broadly cuspidate, while the bracteole is acute to narrowly rounded. The central rachis or strig is thick compared to the strig of the variety Cluster. The cone, and more specifically the bracteoles, contain numerous lupulin glands. As the hop cone matures, the lupulin glands fill with resins and form a globular shapes which are golden yellow in color. One of the most important components of these resins is the alpha-acid which gives beer its bitterness, but other components in the resins of the lupulin glands also contribute to the flavor of the beer.

The cone numbers and cone weight are direct factors in determining the yield of this variety and any other hop variety. Climatic fluctuations, cultural practices, soil type and fertility all have effects on yield by influencing cone numbers and weight. Cone uniformity with regard to size, weight, and stage of maturity varies with the growing season. Cone shape is fairly uniform in the 'H900325-5' variety.

The hop cones of 'H900325-5' variety are well adapted to mechanical harvest because of their compactness and ovoid shape. The cones do not shatter during harvest.

VIII. Growth Characteristics

Growth of the annual stem during a relatively short thirty-five day period is approximately 12–14 feet in length and the extent of this growth is very dependent on temperature, soil conditions and cultural practices.

IV. Variability of Botanical Characteristics

Climatic conditions and cultural practices can cause the dimensions of the various components of a hop plant, including stems, cones, leaves, laterals, and internodes to vary tremendously from one year to the next, from one field to the next within the same year and even from one plant to the next within the same field. These variations produce substantial overlapping of dimensions when comparing varieties and results in these dimensions having little use for comparing varieties.

X. Propagation Methods

Asexual reproduction assures genetic stability and is used for increasing plant rootstock numbers to provide sufficient plants for commercial hop production. Sexual reproduction by plants of this variety is not possible because of its triploid genetic make up. The asexual propagation methodology utilizes 2 inch stem cuttings, which are treated with a rooting hormone and rooted in potting media in greenhouses. The rooted cuttings are grown in greenhouses under controlled conditions.

DETAILED DESCRIPTIVE INFORMATION

Following is a detailed description of the botanical and analytical chemical characteristics of the new variety. The information for this botanical description was either collected or verified during the growing seasons of 1994 through 1996 in the growing areas west of Toppenish and east of Mabton, Wash. These botanical characteristics, and to a lesser degree the analytical chemical characteristics, are somewhat dependent on cultural practices and climatic conditions and can vary with location and season:

1. Parentage: A hop plant originating from a controlled cross pollination between unpatented tetraploid USDA 21055 female hop plant and unpatented Haas male hop plant No. 833-53M.
2. Locality where grown and observed: East of Mabton and West of Toppenish, Wash.
3. Dates of first and last harvest: Approximately August 15 and September 1.
4. Plant characteristics:
   *Plant*.—Green vigorous, climbing vine.
   *Stripe*.—None.
   *Stipule direction*.—Up.
   *Plant shape*.—Columnar.
   *Leaf arrangement*.—Opposite.
   *Number of leaf lobes*.—3 or 5 (mostly 5).
   *Leaf margin*.—Serrate to dentate.
   *Lateral length*.—18 inches average.
   *Internode length*.—6.25 inches average.
   *Leaf width*.—6 inches average.
5. Cone characteristics:
   *Bract tip shape*.—Broadly Cuspidate.
   *Bract tip position*.—Mostly appressed.
   *Bracteole tip shape*.—Acute to narrowly rounded.
   *Compactness*.—Dense tight.
   *Shape*.—Ovoid to conic.
   *Cone length*.—1.75 inches average.
   *Cone tip shape*.—Pointed.
   *Strig*.—Thick.
   *Yield per acre*.—1600–2200 pounds average.
   *Maturity*.—Early.
6. Color characteristics: Fall color characteristics are unknown because the leaves are totally removed and destroyed during the harvesting procedure. Using the Colour Chart of The Royal Horticultural Society of London, Copyrighted 1966, the following color characteristics for H900325-5 have been determined.
   *Leaf upper surface*.—139A.
   *Leaf lower surface*.—147B.
   *Bine*.—146D.
   *Cone bracteole*.—145C.
   *Cone bract*.—137C.
   *Leaf petiole*.—146C.
   *Leaf petiole shading* (*upper surface only*).—183C.
7. Analytical data of cones:
   *% Alpha-Acids* (*bale*).—18–20 (ASBC Spectrophotometric method).
   *% Beta-Acids* (*bale*).—6.0–7.0 (ASBC Spectrophotometric method).
   *Alpha/beta ratio*.—2.8–3.0.
   *Cohumulone* (*% of alpha-acids*).—34.0.
   *Colupulone* (*% of beta-acids*).—59.0.
   *Storage characteristics*.—21.0% transformation after 6 months at 22° C. (Based on USDA Hop Storage Index of baled hops). This rate of transformation is very comparable to that of the commercial varieties Galena and Nugget.
   *Total oils* (*mls*/100 *g*).—Average 2.8.
   *Humulene* (*% of total oils*).—Average 25.0.
   *Caryophyllene* (*% of total oils*).—Average 14.0.
   *Humulene/caryophyllene ratio*.—Average 1.8.
   *Farnesene* (*% of total oils*).—Average 9.0.
   *Myrcene* (*% of total oils*).—Average 28.0.
   *Lupulin* (*% of total cone weight*).—Average 35.0.

* Analytical Data determined on hops with approximately 8% cone moisture.

8. Analytical data of lupulin:
   *% Alpha-acids*.—Average 53.0.
   *% Beta-acids*.—Average 18.0.
9. Disease resistance: The variety 'H900325-5' is moderately susceptible to hop downy mildew fungus, noting that there is no known resistance to the disease in any hop variety. 'H900325-5' is tolerant to strains of Verticillium Wilt and the virus diseases found in the USA grown areas. This variety is also tolerant to the major soil borne pests that affect hops including Phytophthora root rot.
10. Regional adaptation: The 'H900325-5' variety appears to be adapted to both the drier and the more humid growing regions of the United States, specifically including the Yakima Valley of Washington state and the Willamette Valley of Oregon state.
11. Ploidy: The genetic make up of 'H900325-5' is tetraploid USDA 21055×833-53M (21055×63015M). The mother is tetraploid and the father is diploid, thus making H900325-5 a triploid plant. Because the variety is triploid, it is incapable of sexual reproduction. Reproduction can only be asexual.
12. Life expectancy: Life expectancy of this variety is not known, but presumed to be theoretically indefininte similar to other hop varieties of the same species.
13. Use: Flavoring for beers, stouts and ales.
14. Virus and propagation status: 'H900325-5' rootstock has been virus tested and is virus-free. Propagatable plant material exists.

Distinguishing Characteristics

'H900325-5' can be distinguished from all other USA commercial varieties by its semi-dwarf stature, early maturity and high percentage of alpha-acids. No other commercial variety in the USA routinely has alpha-acids of 18–20%. Additionally, 'H900325-5' has a high amount of farnesene as a component in the essential oil (9.0% of total oil is farnesene). The only other USA high alpha-acids variety which has farnesene in the oil is a John I. Haas, Inc. developed variety for which a patent is pending.

I claim:

1. A new variety of hop plant substantially as herein shown and described characterized by the semi-dwarf stature, early maturity and unusually high percentage of alpha-acids in the cones compared to all other commercially available varieties in the USA.

* * * * *